(12) United States Patent
Kitsuyama et al.

(10) Patent No.: US 9,464,095 B2
(45) Date of Patent: Oct. 11, 2016

(54) PRODUCTION METHOD OF HIGH-PURITY NITROGEN-CONTAINING HETEROCYCLIC COMPOUND

(71) Applicant: NISSAN CHEMICAL INDUSTRIES, LTD., Tokyo (JP)

(72) Inventors: Hirohide Kitsuyama, Funabashi (JP); Akihiro Nagaya, Funabashi (JP); Hironobu Yoshino, Funabashi (JP); Ikumasa Hidaka, Sanyo-Onda (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/431,237

(22) PCT Filed: Sep. 27, 2013

(86) PCT No.: PCT/JP2013/076330
§ 371 (c)(1),
(2) Date: Mar. 25, 2015

(87) PCT Pub. No.: WO2014/051077
PCT Pub. Date: Apr. 3, 2014

(65) Prior Publication Data
US 2015/0239899 A1 Aug. 27, 2015

(30) Foreign Application Priority Data
Sep. 27, 2012 (JP) .................................. 2012-215046

(51) Int. Cl.
*C07D 491/052* (2006.01)
(52) U.S. Cl.
CPC ................................ *C07D 491/052* (2013.01)
(58) Field of Classification Search
CPC .............................................. C07D 491/052
USPC ......................................................... 546/89
See application file for complete search history.

(56) References Cited

FOREIGN PATENT DOCUMENTS

| JP | 2007-530436 A | 11/2007 |
| WO | 2005/090357 A1 | 9/2005 |
| WO | 2007/105658 A1 | 9/2007 |

OTHER PUBLICATIONS

Dec. 17, 2013 International Search Report issued in International Application No. PCT/JP2013/076330.
Dec. 17, 2013 Written Opinion issued in International Application No. PCT/JP2013/076330.

*Primary Examiner* — Rita Desai
(74) *Attorney, Agent, or Firm* — Oliff PLC

(57) ABSTRACT

A method for producing a high-purity nitrogen-containing heterocyclic compound includes: a process (a) and a process (b): (a) a process of mixing a mixture containing a compound and as an impurity compound with a solvent and a metal salt, and (b) a process of obtaining a mixture in a solution state in which the content of the compound has decreased compared to that in the mixture in the process (a) by filtering a mixed solution obtained in the process (a), or a process of obtaining a mixture in which the content of the compound has decreased compared to that in the mixture in the process (a) by further evaporating the solvent or crystallizing following the filtering;

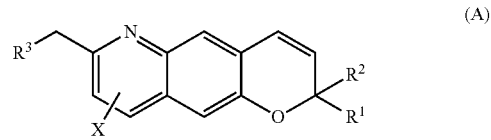

(A)

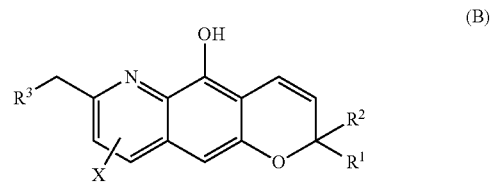

(B)

(where $R^1$ and $R^2$ are each independently a hydrogen atom, a $C_{1-6}$ alkyl group, etc., $R^3$ is a hydrogen atom, a $C_{1-6}$ alkyl group, etc., X is a hydrogen atom, etc.).

15 Claims, No Drawings

PRODUCTION METHOD OF HIGH-PURITY NITROGEN-CONTAINING HETEROCYCLIC COMPOUND

TECHNICAL FIELD

The present invention relates to a method for producing a high-purity nitrogen-containing heterocyclic compound of Formula (A):

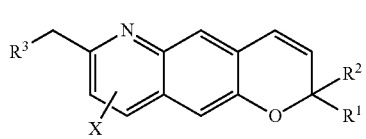

(A)

(where $R^1$ and $R^2$ are each independently a hydrogen atom, a $C_{1-6}$ alkyl group, or a $C_{7-12}$ aralkyl group; $R^3$ is a hydrogen atom, a $C_{1-6}$ alkyl group, a $C_{7-12}$ aralkyl group, or a $C_{1-6}$ acyloxy group; and X is a hydrogen atom, a halogen atom, a $C_{1-6}$ alkyl group, a $C_{3-6}$ cycloalkyl group, a $C_{6-10}$ aryl group, a $C_{7-12}$ aralkyl group, a $C_{1-6}$ alkoxy group, a $C_{1-6}$ acyloxy group, or a cyano group).

BACKGROUND ART (3R*,4S*)-7-hydroxymethyl-2,2,9-trimethyl-4-(phenetylamino)-3,4-dihydro-2H-pyrano[2,3-g]quinolin-3-ol of Formula (3) [compound (3)] exhibits an anti-arrhythmic action and possibility of the compound (3) for using as a medicine is known (for example, see Patent Document 1).

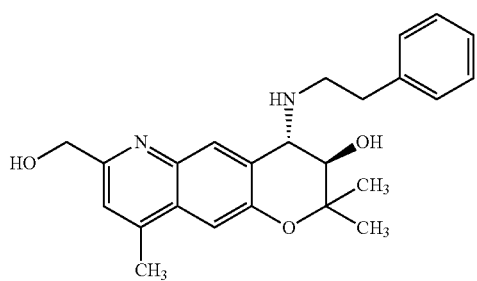

(3)

For synthesizing the compound (3), a reaction path is shown below in which: 2,2,7,9-tetramethyl-2H-pyrano[2,3-g]quinoline [compound (4)] is reacted with m-chloroperoxybenzoic acid and the resultant reaction product is reacted with acetic anhydride to obtain (2,2,9-trimethyl-2H-pyrano[2,3-g]quinolin-7-yl)-methyl acetate [compound (1)]; and the compound (1) is subjected to an asymmetric epoxidation reaction using as a catalyst, an optically active manganese complex (for example, see Patent Document 1) or an optically active titanium complex (for example, see Patent Document 2) to obtain (3R*,4R*)-(3,4-epoxy-2,2,9-trimethyl-3,4-dihydro-2H-pyrano[2,3-g]quinolin-7-yl)-methylacetate [compound (5)].

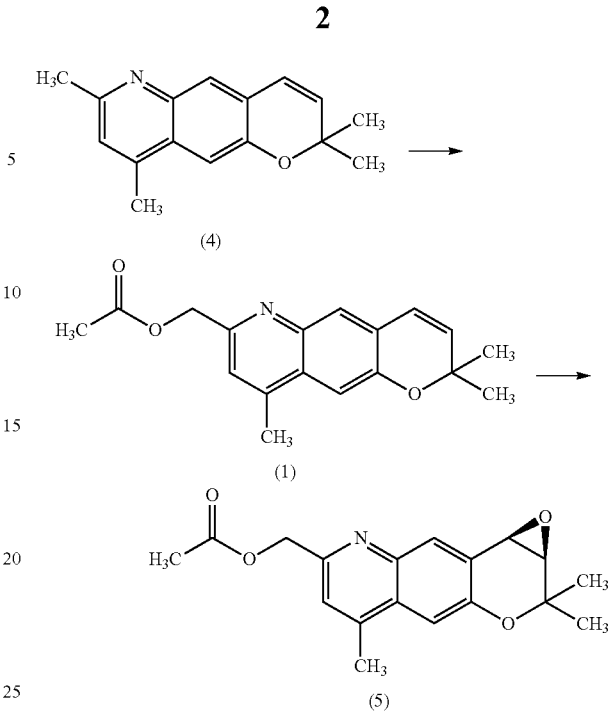

Here, in a reaction using a small amount of a metal complex as a catalyst, there is a probability that the reaction is largely inhibited by a small amount of impurities. Accordingly, in a reaction leading the compound (1) to the compound (5), it is particularly desired that the compound (1) as the reaction substrate is obtained in high purity. As the production method of the compound (1), however, only a method has been known in which after the completion of the reaction, a crude product is purified through silica gel column chromatography, and thus another new production method of the compound (1) available in an industrial scale has been desired.

PRIOR ART DOCUMENTS

Patent Documents

Patent Document 1: WO 2005/090357
Patent Document 2: WO 2007/105658

SUMMARY OF THE INVENTION

Problem to be Solved by the Invention

It is an object of the present invention to provide a method for producing a high-purity nitrogen-containing heterocyclic compound.

Means for Solving the Problem

As a result of assiduous research, the inventors of the present invention have found that when the compound (4) is oxidized and further, the oxidized compound is reacted with an acid anhydride or an acid halide to be led to the compound (1), 5-hydroxy-2,2,7,9-tetramethyl-2H-pyrano[2,3-g]quinoline [compound (2)] in which a quinoline ring part is oxidized is generated as a by-product, and that when the compound (2) and the compound (1) are in a mixed state, in a process in which the compound (1) is led to the compound (5), the compound (2) decomposes a metal complex catalyst used for the reaction to inhibit the reaction progress.

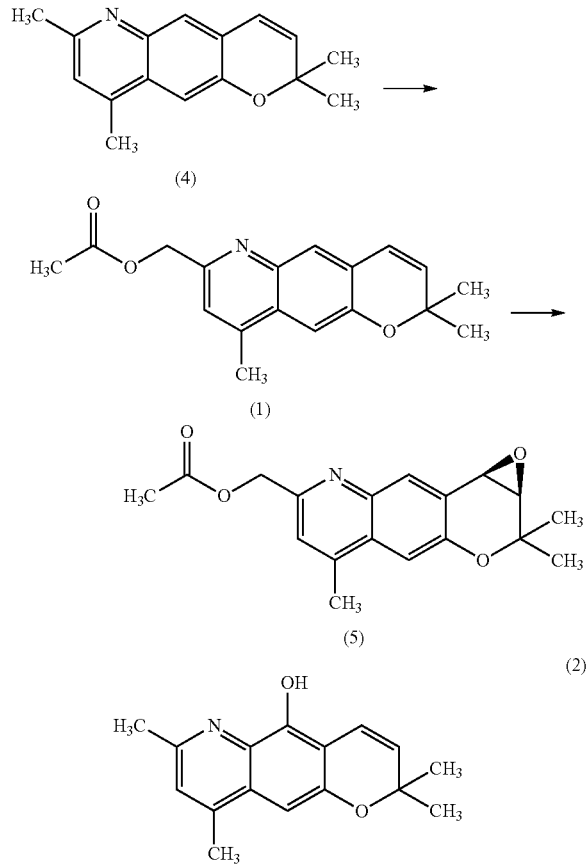

Further, the inventors of the present invention have found a production process capable of removing the compound (2) simply and effectively from the mixture containing the compound (1) and the compound (2) and have completed a production method of the compound (1) having high purity.

Specifically, the present invention is characterized by the following methods:

(I)
a production method of a compound (A) having high purity, comprising: a process (a) and a process (b):
(a) a process of mixing a mixture containing a compound (A):

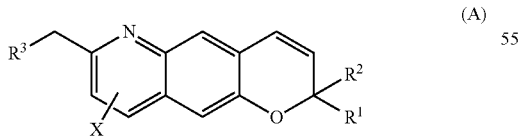

(where $R^1$ and $R^2$ are each independently a hydrogen atom, a $C_{1-6}$ alkyl group, or a $C_{7-12}$ aralkyl group; $R^3$ is a hydrogen atom, a $C_{1-6}$ alkyl group, a $C_{7-12}$ aralkyl group, or a $C_{1-6}$ acyloxy group; and X is a hydrogen atom, a halogen atom, a $C_{1-6}$ alkyl group, a $C_{3-6}$ cycloalkyl group, a $C_{6-10}$ aryl group, a $C_{7-12}$ aralkyl group, a $C_{1-6}$ alkoxy group, a $C_{1-6}$ acyloxy group, or a cyano group) and as an impurity, a compound (B):

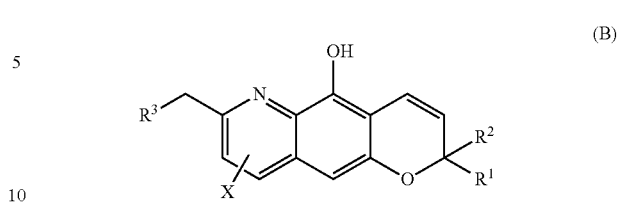

(where $R^1$, $R^2$, $R^3$, and X are the same as defined above) with a solvent and a metal salt, and
(b) a process of obtaining a mixture in a solution state in which the content of the compound (B) has decreased compared to that in the mixture in the process (a) by filtering a mixed solution obtained in the process (a), or a process of obtaining a mixture in which the content of the compound (B) has decreased compared to that in the mixture in the process (a) by further evaporating the solvent or crystallizing following the filtering;
(II)
the production method according to (I), in which the compound (A) is a compound (1):

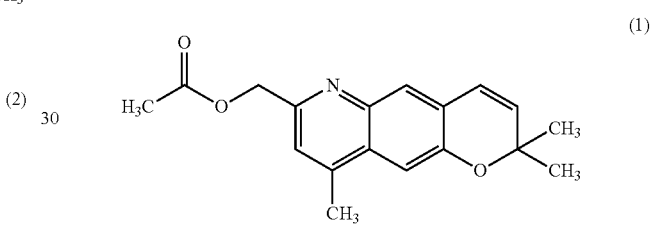

and
the compound (B) is a compound (2):

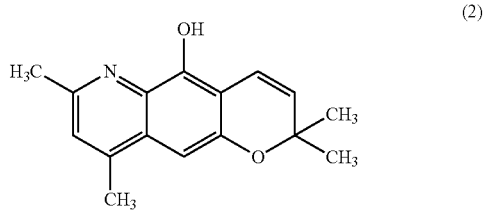

(III)
the production method according to (I) or (II), in which the process (b) is a process (b1) below,
(b1) a process of obtaining a mixture in a solution state in which the content of the compound (B) has decreased compared to that in the mixture in the process (a) by filtering the mixed solution obtained in the process (a) using a filtration auxiliary, or a process of obtaining a mixture in which the content of the compound (B) has decreased compared to that in the mixture in the process (a) by further evaporating the solvent or crystallizing following the filtering;
(IV)
the production method according to (III), in which the filtration auxiliary is silica gel;
(V)
the production method according to any one of (I) to (IV), further comprising: a process (c); and a process (d), after the process (b):

(c) a process of mixing the mixture obtained in the process (b) with a solvent and a porous adsorbent, and (d) a process of obtaining a mixture in a solution state in which the content of the compound (B) has decreased compared to that in the mixture in the process (b) by filtering a mixed solution obtained in the process (c), or a process of obtaining a mixture in which the content of the compound (B) has decreased compared to that in the mixture in the process (b) by further evaporating the solvent or crystallizing following the filtering;

(VI)
the production method according to (V), in which the porous adsorbent is active carbon;

(VII)
the production method according to any one of (I) to (VI), further comprising: a process (e); to a process (g), after the process (d):

(e) a process of mixing the mixture obtained in the process (d) with a solvent and an acid, (f) a process of recovering an acid salt generated in the process (e) by filtration, and (g) a process of obtaining a mixture in a solution state in which the content of the compound (B) has decreased compared to that in the mixture in the process (d) by adding the acid salt obtained in the process (f) to a solvent, further adding an alkaline aqueous solution to neutralize the acid salt, and by removing an aqueous phase containing an alkaline salt of an acid by a phase separation operation, or a process of obtaining a mixture in which the content of the compound (B) has decreased compared to that in the mixture in the process (d) by further evaporating the solvent or crystallizing following the above phase separation operation;

(VIII)
the production method according to (VII), in which the acid is hydrogen chloride, methanesulfonic acid, or oxalic acid;

(IX)
the production method according to any one of (I) to (VIII), in which the metal salt is a copper salt;

(X)
the production method according to (IX), in which the copper salt is copper sulfate;

(XI)
the production method according to any one of (I) to (X), in which the solvent contains at least one solvent selected from the group consisting of an acetic acid ester, an aliphatic hydrocarbon, an aromatic hydrocarbon, an alcohol, and an ether; and (XII)
a production method of a compound (1), comprising: a process (a); to a process (g):

(a) a process of: mixing a solvent mixture of ethyl acetate, hexane, and methanol with a mixture obtained by oxidizing a compound (4):

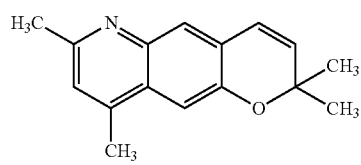

using m-chloroperoxybenzoic acid or Oxone (registered trademark) and by causing the oxidized compound (4) to react with acetic anhydride or acetic acid halide, the mixture containing a compound (1):

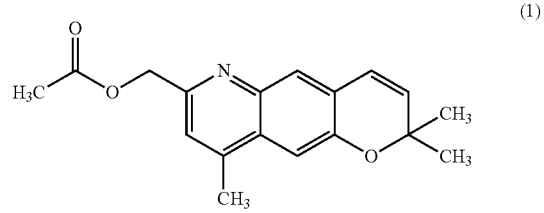 [SMILES: CC(=O)OCc1cc(C)c2cc3c(cc2n1)C=CC(C)(C)O3]

and
as an impurity, a compound (2):

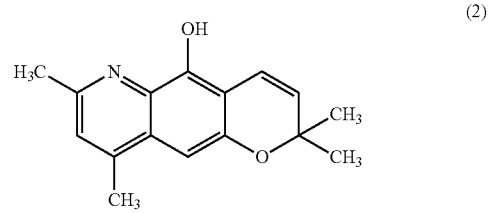

in a content of 3% or more, determined by absorbance analysis at a wavelength of 230 nm; and adding a copper sulfate aqueous solution or copper sulfate anhydride to the resultant mixture to stir the resultant mixture, (b) a process of obtaining a mixture in which the content of the compound (2) has decreased compared to that in the mixture in the process (a) by adding silica gel to the mixed solution obtained in the process (a) to stir the resultant mixture and filtering the mixture, or by passing the mixed solution obtained in the process (a) through a silica gel layer to filter the mixed solution and evaporating a solvent from the mixed solution filtered, (c) a process of mixing the mixture obtained in the process (b) with ethyl acetate and active carbon to stir the resultant mixture, (d) a process of obtaining a mixture in a solution state in which the content of the compound (2) has decreased compared to that in the mixture in the process (b) by filtering a mixed solution obtained in the process (c), (e) a process of adding a solution obtained in the process (d), or a solution obtained by concentrating the solution obtained in the process (d) followed by adding ethyl acetate, to a solution obtained by adding 1-propanol and t-butyl methyl ether to oxalic acid dihydrate and stirring the resultant solution, (f) a process of recovering a salt of oxalic acid generated in the process (e) by filtration, and (g) a process of obtaining a mixture in a solution state in which the content of the compound (2) has decreased compared to that in the mixture in the process (d), by adding the salt of oxalic acid obtained in the process (f) to toluene, further adding a potassium carbonate aqueous solution to neutralize the salt of oxalic acid, and removing an aqueous phase containing potassium oxalate salt by a phase separation operation.

MODES FOR CARRYING OUT THE INVENTION

Hereinafter, the present invention is described more in detail.

The high purity mentioned in the present invention means a state in which the content of the impurity contained in the mixture has decreased compared to that in the mixture before the treatment process.

In the present specification, "n-" means "normal-", "i-" means "iso-", "s-" and "sec-" mean "secondary-", and "t-" and "tert-" mean "tertiary-".

The compound (1) as a raw material of the present invention can be synthesized, for example, by a method described in WO 2005/090357 (Patent Document 1).

The compound (A):

(A)

$R^3$—⟨structure with N, X, O, $R^1$, $R^2$⟩

(where $R^1$ and $R^2$ are each independently a hydrogen atom, a $C_{1-6}$ alkyl group, or a $C_{7-12}$ aralkyl group; $R^3$ is a hydrogen atom, a $C_{1-6}$ alkyl group, a $C_{7-12}$ aralkyl group, or a $C_{1-6}$ acyloxy group; and X is a hydrogen atom, a halogen atom, a $C_{1-6}$ alkyl group, a $C_{3-6}$ cycloalkyl group, a $C_{6-10}$ aryl group, a $C_{7-12}$ aralkyl group, a $C_{1-6}$ alkoxy group, a $C_{1-6}$ acyloxy group, or a cyano group) as a raw material of the present invention can be also synthesized by the method described in Patent Document 1.

The substituent in the present invention is described.

The halogen atom means fluorine, chlorine, bromine, or iodine.

In the concept of the alkyl group in the present invention, the linear alkyl group and the branched alkyl group are included.

The $C_{1-6}$ alkyl group means an alkyl group having a carbon atom number of 1 to 6 and examples thereof include a methyl group, an ethyl group, a n-propyl group, an i-propyl group, a n-butyl group, an i-butyl group, a s-butyl group, a t-butyl group, a n-pentyl group, and a n-hexyl group. Among them, as the $C_{1-6}$ alkyl group, a $C_{1-3}$ alkyl group, that is, an alkyl group having a carbon atom number of 1 to 3 is preferred and a methyl group is more preferred.

The $C_{3-6}$ cycloalkyl group means a cycloalkyl group having a carbon atom number of 3 to 6 and examples thereof include a cyclopropyl group, a cyclobutyl group, and a cyclohexyl group. Among them, as the $C_{3-6}$ cycloalkyl group, a cyclopropyl group is preferred.

The $C_{6-10}$ aryl group means an aryl group having a carbon atom number of 6 to 10 and examples thereof include a phenyl group and a naphthyl group. Among them, as the $C_{6-10}$ aryl group, a phenyl group is preferred.

The $C_{7-12}$ aralkyl group means a group formed by substituting the above-described $C_{1-6}$ alkyl group with one phenyl group. The phenyl group may be substituted at any position on the $C_{1-6}$ alkyl group. Examples of the $C_{7-12}$ aralkyl group include a benzyl group, a phenylethyl group, a phenylpropyl group, and a phenylbutyl group. Among them, as the $C_{7-12}$ aralkyl group, a benzyl group is preferred.

The $C_{1-6}$ alkoxy group means an oxy group substituted with the above-described $C_{1-6}$ alkyl group. Examples thereof include a methoxy group, an ethoxy group, an i-propoxy group, and a t-butoxy group. Among them, as the $C_{1-6}$ alkoxy group, a $C_{1-3}$ alkoxy group, that is, an oxy group substituted with a $C_{1-3}$ alkyl group is preferred and a methoxy group is more preferred.

The $C_{1-6}$ acyloxy group means a carbonyloxy group substituted with the above-described $C_{1-6}$ alkyl group. Examples thereof include an acetoxy group [a $CH_3C(=O)$O— group]. Among them, as the $C_{1-6}$ acyloxy group, an acetoxy group is preferred.

One aspect of the present invention is, as described above, a production method of the compound (A) having high purity including a process (a) below and a process (b) below, (a) a process of mixing a mixture containing a compound (A) and a compound (B) or a mixture containing a compound (1) and a compound (2) with a solvent and a metal salt, and (b) a process of obtaining a mixture in a solution state in which the content of the compound (B) or the compound (2) has decreased compared to that of the compound (B) or the compound (2) in the mixture in the process (a) by filtering the mixed solution obtained in the process (a), or a process of obtaining a mixture in which the content of the compound (B) or the compound (2) has decreased compared to that of the compound (B) or the compound (2) in the mixture in the process (a) by further evaporating the solvent or crystallizing after the filtering.

In the present specification, if necessary,

"The mixture containing the compound (A) and the compound (B)" or "the mixture containing the compound (1) and the compound (2)" described in the process (a) is described as "the mixture before the purification", The process (a) and the process (b) are described as "the metal salt treatment process", and The mixture containing the compound (A) and the compound (B) or the mixture containing the compound (1) and the compound (2) after the metal salt treatment process is described as "the purified product after the metal salt treatment".

The metal salt treatment process can be performed by dissolving or dispersing the mixture before the purification in a solvent.

As the metal salt used, a salt containing copper (monovalent or divalent), cobalt (divalent), manganese (trivalent), or titanium (tetravalent) can be used. Preferred examples thereof include a copper salt and more preferred examples thereof include an anhydride or a hydrate of a halogenide of copper (for example, a chloride, a bromide, and an iodide), a nitrate, a carbonate, a sulfate, a phosphate, an acetate, and the like. Further preferred examples thereof include copper sulfate anhydride, copper sulfate pentahydrate, cupric chloride, cupric bromide, cupric nitrate, cuprous chloride, cuprous bromide, and cupric acetate and particularly preferred examples thereof include copper sulfate anhydride and copper sulfate pentahydrate.

These metal salts may be used individually or in combination of two or more types thereof.

These metal salts may be used either in a solid state or as a solution (for example, an aqueous solution or a methanol solution) thereof In terms of the efficiency as the production method, it is desired to dissolve the metal salt before using the metal salt as a solution.

Although the amount of the metal salt used is not limited so long as the effects of the object of the present invention can be achieved, the metal salt is used in an amount of preferably 0.001 molar equivalent to 1.5 molar equivalent, more preferably 0.005 molar equivalent to 1.0 molar equivalent, and further preferably 0.01 molar equivalent to 0.5 molar equivalent, based on the number of moles of the mixture before the purification.

Although the solvent capable of being used in the metal salt treatment process is not limited so long as the effects of the object of the present invention can be achieved,
water,
alcohol solvents (for example, methanol, ethanol, 1-propanol, and isopropanol),
halogen-containing hydrocarbon solvents (for example, methylene chloride),
ketone solvents (for example, acetone and methyl ethyl ketone),
ester solvents (for example, methyl formate, ethyl formate, methyl acetate, ethyl acetate, propyl acetate, and isopropyl acetate),
aromatic hydrocarbon solvents (for example, benzene, toluene, and xylene),
aliphatic hydrocarbon solvents (for example, hexane and heptane), and
ether solvents (for example, tetrahydrofuran, 1,4-dioxane, and t-butyl methyl ether) are preferably used in terms of effectively performing the purification.

These solvents may be used individually or in combination of two or more types thereof.

In particular, an aliphatic hydrocarbon solvent and an organic solvent miscible with the aliphatic hydrocarbon solvent are used. Specifically, an aliphatic hydrocarbon solvent and an alcohol solvent, an aliphatic hydrocarbon solvent and a halogen-containing hydrocarbon solvent, an aliphatic hydrocarbon solvent and a ketone solvent, an aliphatic hydrocarbon solvent and an ester solvent, an aliphatic hydrocarbon solvent and an aromatic hydrocarbon solvent, an aliphatic hydrocarbon solvent and an ether solvent, or an aliphatic hydrocarbon solvent and an ester solvent and an alcohol solvent are used. More preferably, a single solvent of an ester solvent, a solvent mixture of an aliphatic hydrocarbon solvent and an ester solvent, and a solvent mixture of an aliphatic hydrocarbon solvent, an ester solvent, and an alcohol solvent is used. Particularly preferably, a solvent mixture of hexane, ethyl acetate, and methanol is used.

Although the amount of the solvent used is not particularly limited, it is 0.1 parts by mass to 1,000 parts by mass, more preferably 0.5 parts by mass to 100 parts by mass, and further preferably 1 part by mass to 50 parts by mass, based on the mass of the mixture before the purification.

Although the treatment temperature for the metal salt treatment process is not particularly limited, it is an arbitrary temperature preferably in a range of from 0° C. to a boiling point of the solvent used and more preferably in a range of from 1° C. to 40° C.

Although the treatment time for the metal salt treatment process is not particularly limited, from the viewpoint of the production efficiency, it is preferably up to 24 hours from immediately after the mixture containing the compound (A) and the compound (B) or the mixture containing the compound (1) and the compound (2) is mixed with the metal salt. The treatment time is more preferably from 10 minutes to 10 hours and further preferably from 30 minutes to 3 hours.

In the present invention, for the filtration in the process (b) of the metal salt treatment process, a filtration auxiliary can be used. A representative example of the filtration auxiliary is silica gel.

In the present specification, if necessary, the filtration operation using the filtration auxiliary in the metal salt treatment process is described as "silica gel treatment operation".

After the process (a), when a complex of the mixture before the purification with the metal is filtered, the filtration auxiliary is preferably used.

Although the filtration auxiliary is not limited so long as the effects of the object of the present invention can be achieved, as the filtration auxiliary, preferably used is a granular substance that is not dissolved in each component of the mixture before the filtration, is not chemically reacted with each component of the mixture before the filtration, and can be filtered with a filter medium used for the filtration.

Preferred specific examples of the filtration auxiliary include a particle containing silicon dioxide, a particle containing a silicate, asbestos, and active carbon. More preferred specific examples include silica gel, diatomaceous earth, Celite (registered trademark), talc, zeolite, and active carbon. Further preferred examples thereof include silica gel, diatomaceous earth, and Celite (registered trademark). Particularly preferred is silica gel.

The amount of the filtration auxiliary used is 0.1 part by mass to 5 parts by mass, more preferably 0.5 part by mass to 2 parts by mass, and further preferably 0.5 part by mass to 1 part by mass, based on the mass of the mixture before the purification.

The filtration can be performed either by laying the filtration auxiliary in a filtration apparatus beforehand or by charging the filtration auxiliary into a solution to be filtered.

As described above, although a representative example of the filtration auxiliary is silica gel, the silica gel treatment operation of the present invention differs from the column chromatography in the essential principle, which can be judged from such facts as (i) also by filtering a solution to be filtered after the filtration auxiliary is charged into the solution, a desired effect can be obtained, and (ii) even when filtration is performed after the filtration auxiliary is laid in a filtration apparatus, the filtrate is not fractionated.

Although the treatment temperature for charging the filtration auxiliary into a solution to be filtered is not particularly limited, it is an arbitrary temperature in a range of preferably from 0° C. to a boiling point of the solvent used and more preferably from 1° C. to 40° C.

Although the treatment time for charging the filtration auxiliary into the solution to be filtered is not particularly limited, from the viewpoint of the production efficiency, the treatment time is preferably up to 24 hours from immediately after the mixed solution obtained in the process (a) and the filtration auxiliary are mixed with each other, more preferably from 1 hour to 10 hours.

Although the treatment temperature for the treatment of filtration by laying the filtration auxiliary in a filtration apparatus beforehand is not particularly limited, from the viewpoint of the production efficiency, it is an arbitrary temperature in a range of preferably from 0° C. to a boiling point of the used solvent, more preferably from 0° C. to 50° C., and further preferably from 10° C. to 40° C.

Although the treatment time for the treatment of filtration by laying the filtration auxiliary in a filtration apparatus beforehand is not particularly limited, from the viewpoint of the production efficiency, the treatment time is preferably up to 24 hours from immediately after the mixed solution obtained in the process (a) and the filtration auxiliary are mixed with each other, more preferably from 1 hour to 10 hours.

In the present invention, the purified product after the metal salt treatment can be further treated with a porous adsorbent.

In the present specification, if necessary, the present process is described as "porous adsorbent treatment process", and the mixture containing the compound (A) and the compound (B) or the mixture containing the compound (1) and the compound (2) after the porous adsorbent treatment process, is described as "purified product after porous adsorbent treatment".

The porous adsorbent treatment process can be performed by dissolving or dispersing the purified product after the metal salt treatment in a solvent.

Examples of the porous adsorbent include zeolite, silica gel, alumina, and active carbon and among them, active carbon is preferred.

The amount of the porous adsorbent used is 0.001 part by mass to 1 part by mass, more preferably 0.01 part by mass to 0.5 part by mass, and further preferably 0.05 part by mass to 0.2 part by mass, based on the mass of the mixture before the purification.

Although the solvent capable of being used in the porous adsorbent treatment process is not limited so long as the effects of the object of the present invention can be achieved,
  water,
  alcohol solvents (for example, methanol, ethanol, 1-propanol, and isopropanol),
  halogen-containing hydrocarbon solvents (for example, methylene chloride),
  ketone solvents (for example, acetone and methyl ethyl ketone),
  ester solvents (for example, methyl formate, ethyl formate, methyl acetate, ethyl acetate, propyl acetate, and isopropyl acetate),
  aromatic hydrocarbon solvents (for example, benzene, toluene, and xylene),
  aliphatic hydrocarbon solvents (for example, hexane and heptane), and
  ether solvents (for example, tetrahydrofuran, 1,4-dioxane, and t-butyl methyl ether) are preferably used in terms of effectively performing the purification.

These solvents may be used individually or in combination of two or more types thereof.

In particular, an ester solvent and an organic solvent miscible with the ester solvent are used. Specifically, an ester solvent and an alcohol solvent, an ester solvent and a halogen-containing hydrocarbon solvent, an ester solvent and a ketone solvent, an ester solvent and an aromatic hydrocarbon solvent, an ester solvent and an aliphatic hydrocarbon solvent, or an ester solvent and an ether solvent are used. More preferably, a single solvent of an ester solvent and a solvent mixture of an ester solvent and an aliphatic hydrocarbon solvent are used. Particularly preferably, ethyl acetate is used.

Although the amount of the solvent used is not particularly limited, it is 0.1 part by mass to 1,000 parts by mass, more preferably 0.5 part by mass to 100 parts by mass, and further preferably 1 part by mass to 50 parts by mass, based on the mass of the mixture before the purification.

Although the treatment temperature for the porous adsorbent treatment process is not particularly limited, it is an arbitrary temperature in a range of preferably from 0° C. to a boiling point of the solvent used and more preferably from 1° C. to 40° C.

Although the treatment time for the porous adsorbent treatment process is not particularly limited, from the viewpoint of the production efficiency, the treatment time is preferably up to 24 hours from immediately after the purified product after the metal salt treatment and the porous adsorbent are mixed with each other, more preferably from 1 hour to 10 hours.

In the present invention, the purified product after the porous adsorbent treatment can be further purified by recrystallizing the purified product as an acid salt.

In the present specification, if necessary, the present process is described as "acid treatment process" and an acid salt of the compound (A) or an acid salt of the compound (1) after the acid treatment is described as "purified product after acid treatment".

The acid treatment process can be performed by dissolving or dispersing the purified product after the porous adsorbent treatment in a solvent.

Although the acid capable of being used for the present invention is not limited so long as the effects of the object of the present invention can be achieved, the acid used is hydrochloric acid, methanesulfonic acid, oxalic anhydride, or oxalic acid dihydrate. More preferably, oxalic anhydride or oxalic acid dihydrate is used, and particularly preferably, oxalic acid dihydrate is used.

The amount of the acid used is 1 molar equivalent to 5 molar equivalent and more preferably 1 molar equivalent to 3 molar equivalent, based on the number of moles of the mixture before the purification.

Although the solvent capable of being used in the acid treatment process is not limited so long as the effects of the object of the present invention can be achieved,
  water,
  alcohol solvents (for example, methanol, ethanol, 1-propanol, and isopropanol),
  halogen-containing hydrocarbon solvents (for example, methylene chloride),
  ketone solvents (for example, acetone and methyl ethyl ketone),
  ester solvents (for example, methyl formate, ethyl formate, methyl acetate, ethyl
  acetate, propyl acetate, and isopropyl acetate),
  aromatic hydrocarbon solvents (for example, benzene, toluene, and xylene),
  aliphatic hydrocarbon solvents (for example, hexane and heptane), and
  ether solvents (for example, tetrahydrofuran, 1,4-dioxane, and t-butyl methyl ether) are preferably used in terms of effective performance the purification.

These solvents may be used individually or in combination of two or more types thereof.

In particular, an ester solvent and an organic solvent miscible with the ester solvent are used. Specifically, an ester solvent and an alcohol solvent, an ester solvent and a halogen-containing hydrocarbon solvent, an ester solvent and a ketone solvent, an ester solvent and an aromatic hydrocarbon solvent, an ester solvent and an aliphatic hydrocarbon solvent, an ester solvent and an ether solvent, or an ester solvent and an ether solvent and an alcohol solvent are used. More preferably, a solvent mixture of an ester solvent and an ether solvent and an alcohol solvent are used. Particularly preferably, a solvent mixture of ethyl acetate and t-butyl methyl ether and 1-propanol is used.

Although the amount of the solvent used is not particularly limited, it is 0.1 part by mass to 1,000 parts by mass, more preferably 0.5 part by mass to 100 parts by mass, and further preferably 1 part by mass to 50 parts by mass, based on the mass of the mixture before the purification.

Although the treatment temperature for the acid treatment process is not particularly limited, it is an arbitrary temperature in a range of preferably from −10° C. to a boiling point of the solvent used and preferably from −10° C. to 40° C.

Although the treatment time for the acid treatment process is not particularly limited, from the viewpoint of the production efficiency, the treatment time is preferably up to 48 hours from immediately after the purified product after the porous adsorbent treatment and the acid are mixed with each other, and more preferably from 1 hour to 20 hours.

In the present invention, the purified product after the acid treatment is further neutralized and can be converted back into a free form of the compound (A) or the compound (1).

In the present specification, if necessary, the present process is described as "neutralization process" and the compound (A) or the compound (1) after the neutralization process is described as "final purified product".

The neutralization process can be performed by dissolving or dispersing the purified product after the acid treatment in a solvent.

Although the base capable of being used in the present invention is not particularly limited so long as the effects of the object of the present invention can be achieved, an alkali metal salt is used. Particularly preferably, potassium carbonate is used.

The amount of the base used is 1 molar equivalent to 10 molar equivalent and more preferably 1 molar equivalent to 5 molar equivalent, based on the number of moles of the mixture before the purification.

Although the solvent capable of being used in the neutralization process is not limited so long as the effects of the object of the present invention can be achieved,
water,
alcohol solvents (for example, methanol, ethanol, 1-propanol, and isopropanol),
halogen-containing hydrocarbon solvents (for example, methylene chloride),
ketone solvents (for example, acetone and methyl ethyl ketone),
ester solvents (for example, methyl formate, ethyl formate, methyl acetate, ethyl acetate, propyl acetate, and isopropyl acetate),
aromatic hydrocarbon solvents (for example, benzene, toluene, and xylene),
aliphatic hydrocarbon solvents (for example, hexane and heptane), and
ether solvents (for example, tetrahydrofuran, 1,4-dioxane, and t-butyl methyl ether) are preferably used in terms of effective performance the purification.

These solvents may be used individually or in combination of two or more types thereof.

In particular, an aromatic hydrocarbon solvent and an organic solvent miscible with the aromatic hydrocarbon solvent are used. Specifically, an aromatic hydrocarbon solvent and an alcohol solvent, an aromatic hydrocarbon solvent and a halogen-containing hydrocarbon solvent, an aromatic hydrocarbon solvent and a ketone solvent, an aromatic hydrocarbon solvent and an ester solvent, an aromatic hydrocarbon solvent and an aliphatic hydrocarbon solvent, or an aromatic hydrocarbon solvent and an ether solvent are used. Preferably, a single solvent of an aromatic hydrocarbon solvent and a solvent mixture of an aromatic hydrocarbon solvent and an ester solvent are used. Particularly preferably, toluene is used.

Although the amount of the solvent used is not particularly limited, it is 0.1 part by mass to 1,000 parts by mass, more preferably 0.5 part by mass to 100 parts by mass, and further preferably 1 part by mass to 50 parts by mass, based on the mass of the mixture before the purification.

Although the treatment temperature for the neutralization process is not particularly limited, it is an arbitrary temperature in a range of preferably from 0° C. to a boiling point of the used solvent and more preferably from 1° C. to 40° C.

Although the treatment time for the neutralization process is not particularly limited, from the viewpoint of the production efficiency, the treatment time is preferably up to 24 hours from immediately after the purified product after the acid treatment is neutralized, and more preferably from 1 hour to 10 hours.

EXAMPLES

Hereinafter, the present invention will be further specifically described, referring to Examples, which should not be construed as limiting the scope of the present invention.

In Examples, NMR means nuclear magnetic resonance, HPLC means high performance liquid chromatography, and V/V means volume vs volume.

The purity (content ratio in the case of the impurity) of each compound in the HPLC analysis is expressed by an area percentage method by which a ratio of the object peak area in the total peak area is expressed in percentage.

In Examples, the NMR analysis was performed using ECP300 manufactured by JEOL Ltd. and the melting point measurement was performed using B-545 manufactured by Shibata Scientific Technology Ltd. The HPLC analysis was performed using LC-20A manufactured by Shimadzu Corporation under the conditions below.
Column: CAPCELL PAK C18-UG80 [manufactured by Shiseido Co., Ltd.; diameter: 4.6 mm, length: 150 mm, particle diameter: 5 μm]
Eluent: acetonitrile-0.02 M phosphoric acid buffer solution (pH 2.9), 40:60, V/V
Flow rate: 1.0 mL/min
Column temperature: 40° C.
Detector wavelength: 230 nm and 254 nm The compound (1) is detected at around 17.9 minutes and the compound (2) is detected at around 10.2 minutes. It was confirmed by a change in an area ratio of a peak of the compound (2) detected at 230 nm whether the compound (2) was removed. In addition, the quantitative recovery percentage calculation analysis of the compound (1) was performed at 254 nm using an internal standard calibration curve prepared by using the preparation of the compound (1) and using diethyl phthalate as an internal standard substance.

Synthesis Example

Synthesis of Compound (1)

(2,2,9-trimethyl-2H-pyrano[2,3-g]quinolin-7-yl)-methyl acetate

Acetic anhydride (138 g, 1.35 mol) and chloroform (400 g) were mixed and the resultant mixture was heated to 40° C. to 55° C. Into the mixture, a chloroform (360 g) solution of 2,2,7,9-tetramethyl-2H-pyrano[2,3-g]quinoline 6-oxide (124 g, 0.486 mol) was added dropwise and the resultant mixture was stirred at 40° C. to 55° C. for 30 minutes. The mixture was cooled down to 30° C. and thereto, methanol (200 g) was added, followed by stirring the resultant mixture for 30 minutes. Then, into the mixture, a 10% sodium hydroxide aqueous solution (649 g) was added dropwise and the resultant mixture was stirred for 3 hours, followed by leaving the mixture at rest to subject the mixture to phase separation. To the resultant organic phase, a 2.5% sodium bicarbonate aqueous solution (600 g) and methanol (200 g) were added and the resultant mixture was stirred for 1 hour, followed by leaving the mixture at rest to subject the mixture to phase separation. To the resultant organic phase, water (600 g) and methanol (100 g) were added and the resultant mixture was stirred for 30 minutes, followed by leaving the mixture at rest to subject the mixture to phase separation. The resultant organic phase was filtered through a funnel in which silica gel (200 g) was laid and the filtration cake of silica gel was washed with ethyl acetate. From the obtained filtrate, the solvent was evaporated under reduced pressure to obtain 298 g of an ethyl acetate solution of the compound (1). As a result of the HPLC quantitative analysis, it was confirmed that the ethyl acetate solution of the compound (1) contained 117 g of the compound (1).

The solution was concentrated to dryness, and then, purified by silica gel chromatography to obtain a reference standard of the compound (1) for the HPLC quantitative analysis and a compound (2) (5-hydroxy-2,2,7,9-tetramethyl-2H-pyrano[2,3-g]quinoline). The analysis data of each compound are shown below.

Compound (1)
Appearance: yellow solid
$^1$H-NMR (CDCl$_3$, TMS):
δ (ppm): 1.50 (6H, s), 2.17 (3H, s), 2.60 (3H, s), 5.27 (2H, s), 5.90 (1H, d, J=9.9 Hz), 6.57 (1H, d, J=9.9 Hz), 7.18 (1H, s), 7.23 (1H, s), 7.66 (1H, s)
Melting point: 72° C.
Compound (2)
Appearance: gray solid
$^1$H-NMR (CDCl$_3$, TMS):
δ (ppm): 1.49 (6H, s), 2.52 (3H, s), 2.59 (3H, s), 5.80 (1H, d, J=9.9 Hz), 6.74 (1H, s), 6.91 (1H, d, J=10.9 Hz), 7.02 (1H, s)

Melting point: 120° C.

In the following Example 1 to Example 3 and Comparative Example 1, using, the mixture of the compound (1) and the compound (2) [in the mixture, the content of the compound (2) was 3.61%, which was found as a result of the HPLC analysis] as a raw material, the purification effect of the compound (2) and a recovery percentage of the compound (1) were studied. The recovery percentage was calculated by dividing the mass of the compound (1) after the treatment by the mass of the compound (1) before the treatment. The mass may be a mass quantified by HPLC. In Example 1 to Example 3 and Comparative Example 1, as silica gel, Silica gel 60 (particle diameter: 0.063 to 0.100 mm) manufactured by Merck KGaA was used.

Example 1

To a 25% ethyl acetate solution (8.02 g, 6.73 mmol) containing the compound (1) and the compound (2), methanol (2.00 g) was added and thereto, as a metal salt, a 10% copper sulfate aqueous solution (0.54 g, 0.34 mmol) was added, followed by stirring the resultant mixture at 20° C. for 1 hour. To the mixture, n-hexane (8.03 g) was added and the resultant mixture was stirred for 30 minutes. The mixture was then filtered through a funnel in which silica gel (2.00 g) was laid and a filtration cake of silica gel was washed with a mixed liquid of n-hexane (4.00 g) and ethyl acetate (2.00 g) to obtain a solution containing the compound (1).

The content ratio of the compound (2) measured by the HPLC analysis was before the treatment, 3.61% and after the treatment, 0.23%. The mass of the compound (1) was before the treatment, 2.00 g and after the treatment, 1.98 g. The recovery percentage of the compound (1) was 99.0%.

By the present treatment, with losing little amount of the compound (1), the content of the compound (2) was able to be reduced.

In the same manner as in Example 1, a 25% ethyl acetate solution containing the compound (1) and the compound (2) was treated with each metal salt aqueous solution. The obtained results are shown in Table 1. From the results in Table 1, for each metal salt aqueous solution, the effects of removing the compound (2) was confirmed, and particularly, for a copper salt compound aqueous solution, a cobalt salt compound aqueous solution, and a manganese salt compound aqueous solution, a large effect of removing the compound (2) was confirmed.

TABLE 1

| Metal salt, State | Metal salt equivalent (equivalent) | HPLC relative area % | | Compound (1) quantitative recovery percentage (%) |
|---|---|---|---|---|
| | | Compound (2) | Compound (1) | |
| Crude compound (I) solution | | 3.61 | 75.46 | |
| 10% CuSO$_4$ aqueous solution | 0.05 | 0.23 | 81.08 | 99.0 |
| 10% CuCl$_2$ aqueous solution | | 0.08 | 80.62 | 98.6 |
| 10% CuBr$_2$ aqueous solution | | 0.08 | 79.72 | 97.1 |
| 10% Cu(NO$_3$)$_2$ aqueous solution | | 0.26 | 79.84 | 99.5 |
| 10% MgSO$_4$ aqueous solution | | 3.56 | 75.73 | 99.7 |
| 10% Fe$_2$SO$_4$ aqueous solution | | 3.32 | 78.06 | 99.1 |
| 10% Li$_2$SO$_4$ aqueous solution | | 3.56 | 76.02 | 98.8 |
| 10% MnSO$_4$ aqueous solution | | 3.51 | 75.77 | 99.6 |
| 10% Al$_2$(SO$_4$)$_3$ aqueous solution | | 3.39 | 78.44 | 98.4 |
| 10% Co$_2$SO$_4$ aqueous solution | | 2.75 | 76.28 | 98.6 |
| 10% Cs$_2$SO$_4$ aqueous solution | | 3.37 | 75.50 | 100.9 |
| 10% Mn(acac)$_3$ aqueous solution | | 2.51 | 75.83 | 102.1 |

Example 2

To a 25% ethyl acetate solution (8.01 g, 6.73 mmol) containing the compound (1) and the compound (2), methanol (2.01 g) was added and thereto, a copper sulfate anhydride (0.22 g, 1.35 mmol) in a solid state was added, followed by dispersing and stirring the resultant mixture at 20° C. for 1 hour. To the mixture, n-hexane (8.02 g) was added and the resultant mixture was stirred for 30 minutes. The mixture was then filtered through a funnel in which silica gel (2.03 g) was laid and a filtration cake of silica gel was washed with a mixed liquid of n-hexane (4.00 g) and ethyl acetate (2.01 g) to obtain a solution containing the compound (1).

The content ratio of the compound (2) measured by the HPLC analysis was before the treatment, 3.61% and after the treatment, 0.26%. The mass of the compound (1) was before the treatment, 2.00 g and after the treatment, 1.99 g. The recovery percentage of the compound (1) was 99.3%.

By the present treatment, with losing little amount of the compound (1), the content of the compound (2) was able to be reduced.

In the same manner as in Example 2, a 25% ethyl acetate solution containing the compound (1) and the compound (2) was subjected to a dispersing-stirring treatment using each metal salt (solid or liquid). The obtained results are shown in Table 2. From the results in Table 2, for almost all metal salt compounds, the effects of removing the compound (2) was confirmed, and particularly, for a manganese salt compound (solid dispersing treatment), a copper salt compound (solid dispersing treatment), and a titanium salt compound (liquid dispersing treatment), a large effect of removing the compound (2) was confirmed.

From the solution, the solvent was evaporated under reduced pressure so that the total amount became 60 g. Into another flask, t-butyl methyl ether (80.1 g), 1-propanol (40.1 g), and oxalic acid dihydrate (17.0 g, 135 mmol) were charged and into the resultant mixture, the concentrate after the above evaporation of the solvent was added dropwise at 26° C. The resultant mixture was stirred at the same temperature for 1 hour, cooled down to 5° C. or lower, and stirred at 5° C. or lower for 4 hours. The precipitated crystal was recovered by filtration and the filtration cake was washed with ethyl acetate (40.0 g) twice.

The obtained crystal was suspended in toluene (100 g) and thereto, a 10% potassium carbonate aqueous solution (139 g) was added and the resultant mixture was stirred, left at rest, and separated. To the resultant organic phase, water (100 g) was added and the resultant mixture was stirred, left at rest, and separated. From the resultant organic phase, the solvent was evaporated under reduced pressure to obtain 60.11 g of a toluene solution containing the compound (1).

TABLE 2

| Metal salt, State | Metal salt equivalent (equivalent) | HPLC relative area % Compound (2) | HPLC relative area % Compound (1) | Compound (1) quantitative recovery percentage (%) |
|---|---|---|---|---|
| Crude compound (I) solution |  | 3.61 | 75.46 |  |
| CuSO$_4$ anhydride (solid) | 0.05 | 0.66 | 80.46 | 98.5 |
| CuSO$_4$ anhydride (solid) | 0.20 | 0.26 | 81.43 | 99.3 |
| CuCl (solid) |  | 0.08 | 79.00 | 95.2 |
| CuBr (solid) |  | 0.38 | 78.85 | 94.2 |
| Cu(OH)$_2$ (solid) |  | 3.63 | 75.97 | 101.1 |
| Cu(OAc)$_2$ (solid) |  | 0.45 | 78.67 | 94.8 |
| Ag$_2$SO$_4$ (solid) |  | 3.68 | 75.97 | 98.7 |
| CuCl$_2$ (solid) |  | 0.04 | 81.92 | 73.8 |
| Mn(acac)$_3$ (solid) |  | 1.36 | 76.57 | 97.9 |
| Ti(OiPr)$_4$ (liquid) |  | 0.30 | 77.42 | 95.1 |
| Ti(OiPr)$_4$ (liquid) | 0.05 | 2.69 | 75.82 | 101.5 |

Example 3

To a 25% ethyl acetate solution (80.0 g, 67.3 mmol) containing the compound (1) and the compound (2), methanol (20.0 g) was added and thereto, a 10% copper sulfate aqueous solution (5.37 g, 3.36 mmol) was added, followed by stirring the resultant mixture at 20° C. for 1 hour. To the mixture, n-hexane (80.0 g) was added and the resultant mixture was stirred for 30 minutes. The mixture was then filtered through a funnel in which silica gel (20.1 g) was laid and a filtration cake of silica gel was washed with a mixed liquid of n-hexane (40.0 g) and ethyl acetate (20.0 g) to obtain a solution containing the compound (1).

The content ratio of the compound (2) measured by the HPLC analysis was before the treatment, 3.61% and after the treatment, 0.21%. The mass of the compound (1) was before the treatment, 20.00 g and after the treatment, 19.80 g. The recovery percentage of the compound (1) was 99.0%.

From this solution, the solvent was evaporated under reduced pressure and thereto, ethyl acetate (140 g) was added, followed by evaporating the solvent again and the resultant solution mass became 120 g. Thereto, active carbon (2.02 g) was added and the resultant solution was stirred at 19° C. for 1 hour. Active carbon was filtered and further, a filtration cake of active carbon was washed with ethyl acetate (60.0 g) to obtain a solution containing the compound (1).

The content ratio of the compound (2) measured by the HPLC analysis after the treatment was 0.07%.

The content ratio of the compound (2) measured by the HPLC analysis was after the treatment, 0.02%. The mass of the compound (1) was after the treatment, 17.46 g. The recovery percentage of the compound (1) was 87.3%.

By the present treatment, while most of the amount of the compound (1) was able to be recovered, the content of the compound (2) was able to be reduced to about 1/180.

Comparative Example 1

To a 25% ethyl acetate solution (80.0 g, 67.3 mmol) containing the compound (1) and the compound (2), methanol (20.0 g) was added and the resultant mixture as it was was stirred at 20° C. for 1 hour. To the mixture, n-hexane (80.0 g) was added and the resultant mixture was stirred for 30 minutes, followed by filtering the mixture through a funnel in which silica gel (20.0 g) was laid. Further, the filtration cake of silica gel was washed with a liquid mixture of n-hexane (40.0 g) and ethyl acetate (20.0 g) to obtain a solution containing the compound (1).

The content of the compound (2) measured by the HPLC analysis was before the treatment, 3.61% and after the treatment, 3.42%. The mass of the compound (1) was before the treatment, 20.00 g and after the treatment, 19.68 g. The recovery percentage of the compound (1) was 98.4%.

From this solution, the solvent was evaporated under reduced pressure and thereto, ethyl acetate (140.0 g) was added, followed by evaporating the solvent again under reduced pressure so that the solution mass became 120 g.

Thereto, active carbon (2.00 g) was added and the resultant solution was stirred at 21° C. for 1 hour. Active carbon was removed by filteration and further, a filtration cake of active carbon was washed with ethyl acetate (60.0 g) to obtain a solution containing the compound (1).

The content ratio of the compound (2) measured by the HPLC analysis was after the treatment, 3.42%. The mass of the compound (1) was after the treatment, 19.68 g.
The recovery percentage of the compound (1) was 98.4%.

From the solution, the solvent was evaporated under reduced pressure so that the total amount became 60.0 g. Into another flask, t-butyl methyl ether (80.0 g), 1-propanol (40.0 g), and oxalic acid dihydrate (17.0 g, 135 mmol) were charged and into the resultant mixture, the concentrate after the above evaporation of the solvent was added dropwise at 25° C. The resultant mixture was stirred at the same temperature for 1 hour, cooled down to 5° C. or lower, and stirred at 5° C. or lower for 4 hours. The precipitated crystal was filtered and the crystal was washed with ethyl acetate (40.0 g) twice.

The obtained crystal was suspended in toluene (100 g) and thereto, a 10% potassium carbonate aqueous solution (139 g) was added and the resultant mixture was stirred, left at rest, and separated. To the resultant organic phase, water (100 g) was added and the resultant mixture was stirred, left at rest, and separated. From the resultant organic phase, the solvent was evaporated under reduced pressure to obtain 60.11 g of a toluene solution containing the purified compound (1).

The content ratio of the compound (2) measured by the HPLC analysis was after the treatment, 1.79%. The mass of the compound (1) was after the treatment, 17.82 g.
The recovery percentage of the compound (1) was 89.1%.

Test Example

Using the compound (1) obtained in Example 3 and the compound (1) obtained in Comparative Example 1 as a raw material, an asymmetric epoxidation reaction with an optically active titanium-salan complex described in Patent Document 2 was performed, so that the reactivities of these two compounds (1) were compared with each other.

The optically active titanium-salan complex was prepared, for example, by a method described in WO 2007/105658 (Patent Document 2) from 3-{([{(1S,2S)-2-[{2-hydroxy-2'-methoxy(1,1'-biphenyl)-3-yl}methyl] amino}cyclohexyl]amino)methyl]-2'-methoxy-(1,1'-biphenyl)-2-ol and titanium tetraisopropoxide.

The evaluation of the reactivity was performed by comparing the reaction conversion rates obtained by dividing a peak area of (3R*,4R*)-(3,4-epoxy-2,2,9-trimethyl-3,4-dihydro-2H-pyrano[2,3-g]quinolin-7-yl)-methylacetate as a reaction product detected by the HPLC analysis performed during the reaction, by the sum of a peak area of the compound (1) as a raw material and a peak area of the reaction product.

(1) To the 20% toluene solution (50.0 g, 33.6 mmol) of the compound (1) obtained in Example 3, a solution of an optically active titanium-salan complex (in an amount corresponding to 0.37 mmol) was added and into the resultant mixture, a 30% hydrogen peroxide water (7.64 g, 67.3 mmol) to which sodium acetate (0.28 g) was added was added dropwise at 26° C. to 27° C. and was reacted at 25° C. to 26° C. for 7 hours. The changes of the reaction conversion rate obtained as a result of the above reaction are summarized in Table 3. The reaction progression was good and the reaction conversion rate exceeded 90%.

TABLE 3

| Reaction time (hour(s)) | Reaction conversion rate (%) |
| --- | --- |
| 1 | 49.0 |
| 2 | 59.4 |
| 3 | 71.2 |
| 4 | 79.6 |
| 5 | 86.5 |
| 6 | 89.8 |
| 7 | 92.4 |

(2) To the 20% toluene solution (50.0 g, 33.6 mmol) of compound (1) obtained in Comparative Example 1, a solution of an optically active titanium-salan complex (in an amount corresponding to 0.37 mmol) was added and into the resultant mixture, a 30% hydrogen peroxide water (7.64 g, 67.4 mmol) to which sodium acetate (0.28 g) was added was added dropwise at 26° C. and was reacted at 25° C. to 26° C. for 23 hours.

The changes of the reaction conversion rate obtained as a result of the above reaction are summarized in Table 4. For the reaction, the reaction conversion rate did not reach even 70% and the reaction progression was poor.

TABLE 4

| Reaction time (hour(s)) | Reaction conversion rate (%) |
| --- | --- |
| 1 | 39.9 |
| 2 | 49.1 |
| 3 | 55.7 |
| 4 | 59.6 |
| 5 | 63.3 |
| 6 | 62.8 |
| 7 | 64.5 |
| 8 | 66.4 |
| 22 | 68.0 |
| 23 | 68.2 |

INDUSTRIAL APPLICABILITY

The present invention provides a method for producing a high-purity nitrogen-containing heterocyclic compound.

The invention claimed is:

1. A production method of a compound (A) having high purity, comprising:

a process (a); and a process (b):

(a) a process of mixing a mixture containing a compound (A):

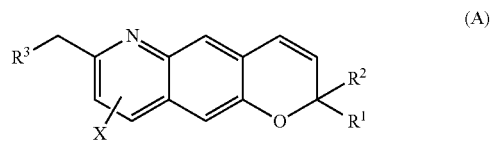

(A)

where $R^1$ and $R^2$ are methyl groups; $R^3$ is a hydrogen atom, a $C_{1-6}$ alkyl group, or a $C_{1-6}$ acyloxy group; and X is a hydrogen atom, a halogen atom, or a $C_{1-6}$ alkyl group, and as an impurity, a compound (B):

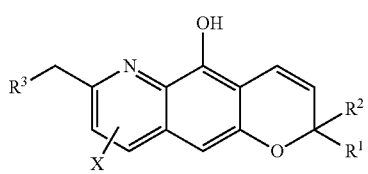

where $R^1$, $R^2$, $R^3$, and X are the same as defined above, with a solvent and a metal salt, and
(b) a process of obtaining a mixture in a solution state in which the content of the compound (B) has decreased compared to that in the mixture in the process (a) by filtering a mixed solution obtained in the process (a), or a process of obtaining a mixture in which the content of the compound (B) has decreased compared to that in the mixture in the process (a) by further evaporating the solvent or crystallizing following the filtering;
wherein the solvent is an alcohol, a halogen-containing hydrocarbon, a ketone, an ester, an aromatic hydrocarbon, an aliphatic hydrocarbon, or an ether; and
the metal salt is a copper salt, a cobalt salt, a manganese salt, a titanium salt, a magnesium salt, an iron salt, a lithium salt, an aluminum salt, a cesium salt, or a silver salt.

2. The production method according to claim 1, wherein the compound (A) is a compound (1):

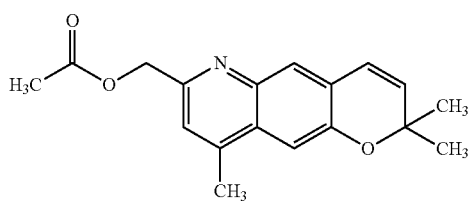

and
the compound (B) is a compound (2)

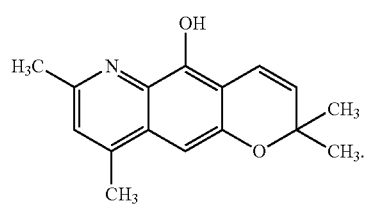

3. The production method according to claim 1, wherein the process (b) is a process (1):
(b 1) a process of obtaining a mixture in a solution state in which the content of the compound (B) has decreased compared to that in the mixture in the process (a) by filtering the mixed solution obtained in the process (a) using a filtration auxiliary, or a process of obtaining a mixture in which the content of the compound (B) has decreased compared to that in the mixture in the process (a) by further evaporating the solvent or crystallizing following the filtering.

4. The production method according to claim 3, wherein the filtration auxiliary is silica gel.

5. The production method according to claim 1, further comprising:
a process (c); and
a process (d),
after the process (b):
(c) a process of mixing the mixture obtained in the process (b) with a solvent and a porous adsorbent, and
(d) a process of obtaining a mixture in a solution state in which the content of the compound (B) has decreased compared to that in the mixture in the process (b) by filtering a mixed solution obtained in the process (c), or a process of obtaining a mixture in which the content of the compound (B) has decreased compared to that in the mixture in the process (b) by further evaporating the solvent or crystallizing following the filtering.

6. The production method according to claim 5, wherein the porous adsorbent is active carbon.

7. The production method according to claim 6, further comprising:
a process (e); to a process (g),
after the process (d):
(e) a process of mixing the mixture obtained in the process (d) with a solvent and an acid,
(f) a process of recovering an acid salt generated in the process (e) by filtration, and
(g) a process of obtaining a mixture in a solution state in which the content of the compound (B) has decreased compared to that in the mixture in the process (d) by adding the acid salt obtained in the process (f) to a solvent, further adding an alkaline aqueous solution to neutralize the acid salt, and removing an aqueous phase containing an alkaline salt of an acid by a phase separation operation, or a process of obtaining a mixture in which the content of the compound (B) has decreased compared to that in the mixture in the process (d) by further evaporating the solvent or crystallizing following the above phase separation operation.

8. The production method according to claim 7, wherein the acid is hydrogen chloride, methanesulfonic acid, or oxalic acid.

9. The production method according to claim 1, wherein the metal salt is a copper salt.

10. The production method according to claim 9, wherein the copper salt is copper sulfate.

11. The production method according to claim 1, wherein the solvent contains at least one solvent selected from the group consisting of an acetic acid ester, an aliphatic hydrocarbon, an aromatic hydrocarbon, an alcohol, and an ether.

12. A production method of a compound (1), comprising:
a process (a); to
a process (g):
(a) a process of: mixing a solvent mixture of ethyl acetate, hexane, and methanol with a mixture obtained by oxidizing a compound (4):

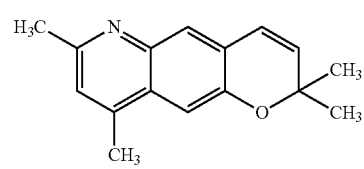

using m-chloroperoxybenzoic acid or Oxone (registered trademark) and by causing the oxidized compound (4) to react with acetic anhydride or acetic acid halide, the mixture containing a compound (1):

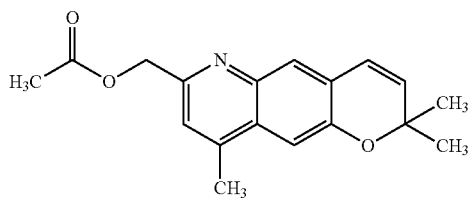
(1)

and
as an impurity, a compound (2):

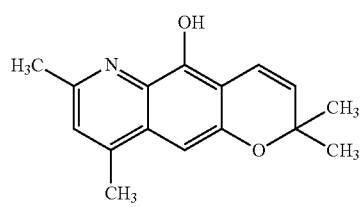
(2)

in a content of 3% or more, determined by absorbance analysis at a wavelength of 230 nm;
and adding a copper sulfate aqueous solution or copper sulfate anhydride to the resultant mixture to stir the resultant mixture,
(b) a process of obtaining a mixture in which the content of the compound (2) has decreased compared to that in the mixture in the process (a) by adding silica gel to the mixed solution obtained in the process (a) to stir the resultant mixture and filtering the mixture, or by passing the mixed solution obtained in the process (a) through a silica gel layer to filter the mixed solution and evaporating a solvent from the mixed solution filtered,
(c) a process of mixing the mixture obtained in the process (b) with ethyl acetate and active carbon to stir the resultant mixture,
(d) a process of obtaining a mixture in a solution state in which the content of the compound (2) has decreased compared to that in the mixture in the process (b) by filtering a mixed solution obtained in the process (c),
(e) a process of adding a solution obtained in the process (d), or a solution obtained by concentrating the solution obtained in the process (d) followed by adding ethyl acetate, to a solution obtained by adding 1-propanol and t-butyl methyl ether to oxalic acid dihydrate and stirring the resultant solution,
(f) a process of recovering a salt of oxalic acid generated in the process (e) by filtration, and (g) a process of obtaining a mixture in a solution state in which the content of the compound (2) has decreased compared to that in the mixture in the process (d), by adding the salt of oxalic acid obtained in the process (f) to toluene, further adding a potassium carbonate aqueous solution to neutralize the salt of oxalic acid, and removing an aqueous phase containing potassium oxalate salt by a phase separation operation.

13. The production method according to claim 1, wherein the metal salt is a copper salt, a cobalt salt, a manganese salt, or a titanium salt.

14. The production method according to claim 1, wherein the solvent contains at least one solvent selected from the group consisting of ethyl acetate, n-hexane, methanol, 1-propanol, toluene, and t-butyl methyl ether.

15. A production method of a compound (A) having high purity, comprising:
a process (a); and
a process (b):
(a) a process of mixing a mixture containing a compound (1):

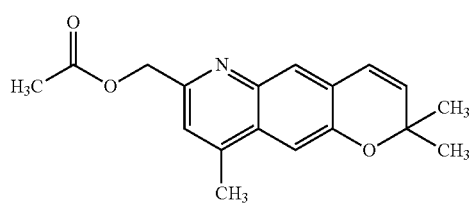
(1)

and as an impurity, a compound (2):

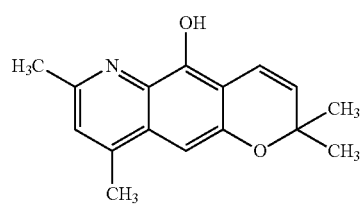
(2)

with a solvent and a metal salt, and
(b) a process of obtaining a mixture in a solution state in which the content of the compound (2) has decreased compared to that in the mixture in the process (a) by filtering a mixed solution obtained in the process (a), or a process of obtaining a mixture in which the content of the compound (2) has decreased compared to that in the mixture in the process (a) by further evaporating the solvent or crystallizing following the filtering.

* * * * *